United States Patent [19]

Penney et al.

[11] Patent Number: 4,848,361

[45] Date of Patent: Jul. 18, 1989

[54] NOCTURNAL PENILE TUMESCENCE AND RIGIDITY MONITOR WITH REMOVABLE LOOPS

[75] Inventors: Richard C. Penney, El Toro, Calif.; Thomas R. Kukowski, Brooklyn Park, Minn.; Stephen K. Sundquist, Chanhassen, Minn.; Charles J. Mike, Woodbury, Minn.

[73] Assignee: Dacomed Corporation, Minneapolis, Minn.

[21] Appl. No.: 144,595

[22] Filed: Jan. 11, 1988

Related U.S. Application Data

[63] Continuation of Ser. No. 821,243, Jan. 22, 1986, abandoned.

[51] Int. Cl.[4] .............................................. A61B 5/00
[52] U.S. Cl. .................................. 128/774; 128/694; 128/782
[58] Field of Search .................. 128/694, 774, 782; 33/511, 512

[56] References Cited

U.S. PATENT DOCUMENTS

| | | |
|---|---|---|
| 3,934,267 | 1/1976 | Kosaka et al. . |
| 3,945,371 | 3/1976 | Adelman .................................. 128/6 |
| 4,103,678 | 8/1978 | Karacan et al. . |
| 4,274,424 | 6/1981 | Kimura et al. . |
| 4,325,383 | 4/1982 | Lacks . |
| 4,333,475 | 6/1982 | Moreno et al. . |
| 4,428,385 | 1/1984 | Morales . |
| 4,469,108 | 9/1984 | Goldstein . |
| 4,474,187 | 10/1984 | Timm et al. . |
| 4,515,166 | 5/1985 | Timm .................................. 128/694 |
| 4,572,211 | 2/1986 | Sagalowsky ......................... 128/774 |
| 4,606,353 | 8/1986 | Timm .................................. 128/774 |
| 4,647,039 | 3/1987 | Noffsinger .......................... 272/136 |

OTHER PUBLICATIONS

Sexual Instrumentation, John L. Semmlow, *IEEE Transactions on Biomedical Engineering*, vol. BME-30, No. 6, Jun. 1983.

U.S. Patent Application, Ser. #590,542, filed Mar. 19, 1984.

"A Simple and Inexpensive Transducer for Quantitative Measurements of Penile Erection During Sleep" *Behavior Research Methods and Instrumentation*, vol. 1, pp. 251-252, Ismet Karacan.

"Some Characteristics of Nocturnal Penile Tumescence in Young Adults" *Archives General Psychiatry*, vol. 26, pp. 351-356, 1972, Ismet Karacan.

"Sleep Related Penile Tumescence as a Function of Age" *American Journal of Psychiatry*, vol. 132, pp. 932-937, 1975, Ismet Karacan.

"Nocturnal Penile Tumescence Monitoring with Stamps" *Urology*, vol. 15, pp. 171-172, 1980, John M. Barry, M.D., Bruce Blank, M.D. and Michael Boileau, M.D.

"Normative Studies on a New Device for Evaluation of Nocturnal Penile Tumescence" *Notice of American Urological Association, Inc. 77th Annual Meeting*, presented by Dr. Alvaro Morales.

Brochure for "Erectiometer" manufactured by Walter Koss Ohg.

"The Role of the Sleep Laboratory in Diagnosis and Treatment, of Impotence" *Sleep Disorders: Diagnosis and Treatment*, ed. by R. L. Williams and I. Karacan, Chapter 14, pp. 365-366, 1978.

Brochure for Rigidimeter (France).

"New Method for Continuous Measurement of Nocturnal Penile Tumescence and Rigidity", Bradley et al., *Urology*, Jul. 1985, vol. XXVI, No. 1.

*Primary Examiner*—Leo P. Picard
*Attorney, Agent, or Firm*—Merchant, Gould, Smith, Edell, Welter & Schmidt

[57] ABSTRACT

A penile rigidity and tumescence monitor and apparatus including a transducer apparatus (20) for providing output signals indicative of penile rigidity and tumescence throughout a penile tumescent event. A control apparatus (22) being operatively interconnected to the transducer apparatus (20) for providing control thereover. A control apparatus (22) also provides for acquisition and storage of penil rigidity and tumescence data represented by the output signals received from the transducer apparatus (20). The transducer apparatus (20) includes readily detachable loop-like portions (38) enabling replacement of the loop-like portions (38).

11 Claims, 6 Drawing Sheets

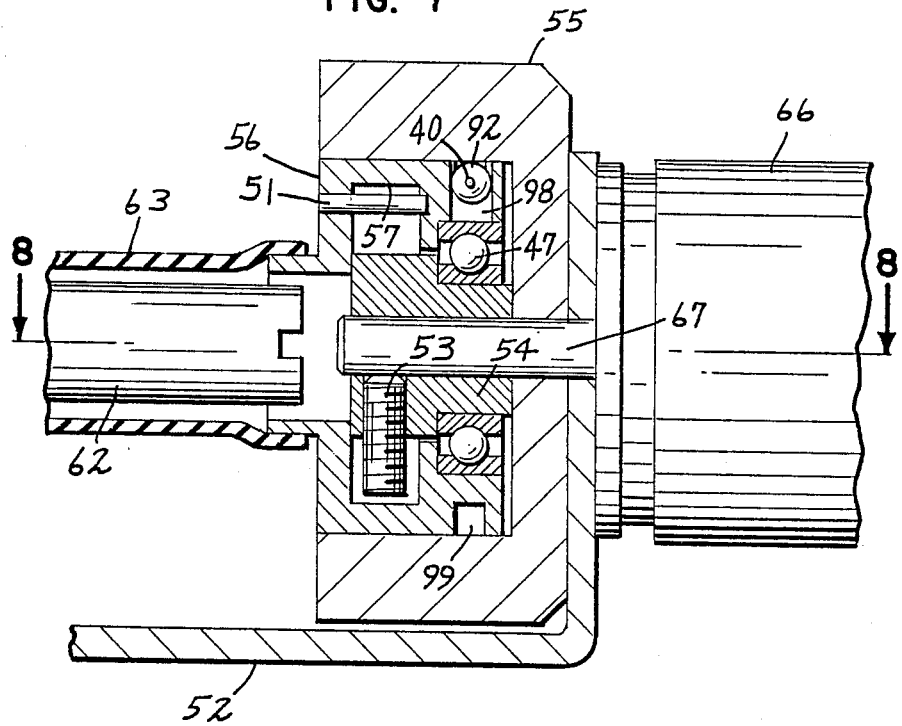
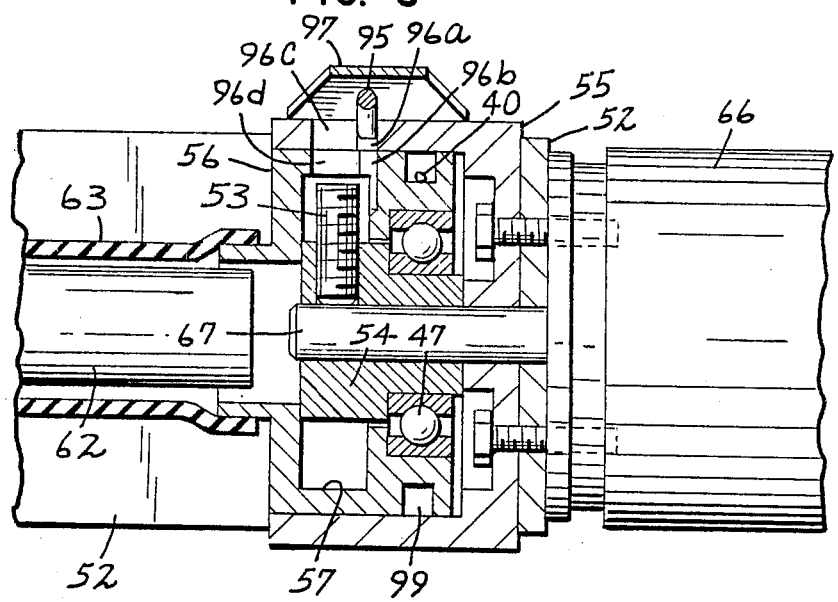

NOCTURNAL PENILE TUMESCENCE AND RIGIDITY MONITOR WITH REMOVABLE LOOPS

This is a continuation of application Ser. No. 821,243, filed Jan. 22, 1986, now abandoned.

BACKGROUND OF THE INVENTION

The present invention relates to a nocturnal penile tumescence and rigidity monitor. More particularly, the present invention relates to a nocturnal penile tumescence and rigidity monitor including detachable loops.

As previously indicated in Ser. No. 318,373, filed Nov. 5, 1981, and U.S. Pat. No. 4,474,187, studies have shown that men with psychogenic impotence generally have normal sleep erections, whereas men with organic impotence have sleep erections that correspond to their impaired wake performance. Such studies have alerted the scientific community of the potential usefulness of nocturnal penile tumescence monitoring in the differential diagnosis of sexual impotence. As a result of the recognition that nocturnal penile tumescence monitoring can be of assistance in diagnosing male erectile impotence, various types of devices and techniques for conducting such monitoring have been developed.

In an article entitled "A Simple and Inexpensive Transducer for Quantitative Measurement of Penile Erection During Sleep", Behavior Research Methods Methods and Instrumentation, Volume 1, pages 251-252, 1969, Ismet Karacan describes a mercury strain-gauge transducer for detecting penile erection. The transducer device is an elastomeric mercury filled tube which is suitably connected to a Wheatstone Bridge and amplifier circuit for recording purposes. As the transducer changes size during penile erection, its electrical resistance changes thereby causing the amplified output from the Wheatstone Bridge to change. The amplified changes in the output are recorded enabling penile activity to be recorded.

In an article entitled "Some Characteristics of Nocturnal Penile Tumescence in Young Adults", Archives General Psychiatry, Volume 26, pages 351-356, 1972, Ismet Karacan et al. describes the normative characteristics of nocturnal penile tumescence (NPT) in a group of 20 to 26 year old men who were measured during continuous all-night recording utilizing the mercury strain-gauge transducer.

Additionally, a number of devices and procedures for monitoring penile tumescence during sleep are noted and referenced in an article entitled "Sleep Related Penile Tumescence as a Function of Age", American Journal of Psychiatry, Volume 132, page 9, September 1975.

In U.S. Pat. No. 4,103,678 issued to Ismet Karacan et al. an apparatus is disclosed for recording minute variations in mercury strain-gauge transducers positioned at the base and the tip of the penis.

The above-referenced materials relate to nocturnal penile tumescence activity and not to the measurement of penile rigidity or hardness during the tumescent event. While it is recognized that nocturnal penile tumescence activity is important to the evaluation of organic impotence, another significant aspect in evaluating organic impotence is the quality of rigidity or hardness achieved during the penile tumescent event.

The mercury strain-gauges described by Ismet Karacan provide a measurement of the change in penile size during a penile tumescent event by changing their impedance as they expand and contract with variations in the penis circumference. The mercury strain-gauges do not, however, provide for measurement of penile rigidity or hardness since the strain-gauges are very elastomeric. A very slight amount of force will fully expand the strain-gauges just as would a larger amount of force.

In addition, the mercury strain-gauge necessitates a rather elaborate monitoring mechanism. The monitoring normally must occur in a health care facility under the supervision of trained professionals. This requires that the patient may be in the health care facility overnight and be subjected to fairly elaborate testing. In addition to creating a substantial imposition on the patient's daily routine, substantial expense is associated with the support facilities and support personnel required to obtain valid test results.

In an article entitled "Nocturnal Penile Tumescence Monitoring with Stamps", Urology, Volume 15, pages 171-172, 1980, a stamp technique is described for detecting complete nocturnal erection for the evaluation of impotence. In this technique, a strip of four postage type stamps is wrapped snuggly around the penis, and the overlapping stamp is moistened to provide a one half to one stamp overlapping seal. The nocturnal penile tumescent stamps, each one and one quarter by one inch, are made on ten by eight inch sheets of paper having water base glue on the opposite side. The patients or subjects are able to perform the evaluations at home rather than go to the hospital, resulting in substantial financial savings. The article indicated that three nights of inhospital nocturnal penile tumescence testing including direct observation of indicated erections and physicians professional fee, currently cost roughly $500. The stamp testing method costs $7.50 for three nights of outpatient testing.

The stamps have a tendency to release after being wetted and stuck together. In addition, the force required to break the perforations between adjacent stamps varies substantially. Thus, the above described stamp technique does not provide a method for detecting a predetermined penile rigidity or hardness.

In Ser. No. 318,373 and U.S. Pat. No. 4,474,187, there is disclosed threshold penile rigidity measuring devices which provide for accurate measurement of a predetermined penile rigidity during a penile tumescence event. However, while these devices provide a safe, simple, accurate and reproducible test which can be used at home to provide a very effective tool in the evaluation of impotence, they do not provide for measuring and recording of penile rigidity at various times throughout the tumescence events and accordingly do not provide any record or indication of the duration which the rigidity is maintained. These devices included a ring-like structure having an attachment mechanism for releasably attaching the ring-like structure to a penis. Associated with the ring-like structure is an apparatus for detecting a predetermined force in the penile tumescent event.

In U.S. Pat. No. 4,515,166 and Ser. No. 713,452, filed Mar. 19, 1985, there is disclosed a penile rigidity and tumescence monitor apparatus comprising transducer means for providing output signals indicative of penile rigidity and tumescence. Operatively associated with the transducer means is control means for providing control of the transducer means. The control means provides further for the acquisition of the output signals from the transducer means and storage of penile rigidity and tumescence data represented by the output signals.

In one embodiment, the penile rigidity and tumescence monitor included a portable housing having an elongated, non-distensible, flexible member extending therefrom. The elongated member was constructed and arranged to form a loop-like portion at a first end, the loop-like portion being adapted for releasably encircling a penis about the circumference thereof. The elongated member was further slidably enclosed within a flexible, non-compressible conduit between the loop-like portion and the housing, the non-compressible conduit being suitably attached to the housing. Should the loop-like portion, and/or the elongated member be damaged, the nocturnal penile tumescence and rigidity monitor must be serviced at the factory. This results in lost time and is rather costly. Moreover, in typical usage, the loop-like portions are used many times over, being disinfected between uses. In view of the public's concern with cross contamination, this could negatively affect the usage of the tumescence and rigidity monitor. Moreover, the patient might potentially be exposed to transmission of disease from one patient to the next if the loop-like portions are not properly cleaned. Additionally, after a period of time, a loss of loop performance is detected.

The present invention overcomes these and many other problems associated with currently available devices.

SUMMARY OF THE INVENTION

The present invention relates to a penile rigidity and tumescence monitor apparatus comprising transducer means for providing output signals indicative of penile rigidity and tumescence. Operatively associated with the transducer means is control means for providing control of the transducer means. The transducer means includes readily interchangeable loop-like portions adapted for releasably encircling a penis about the circumference thereof.

In one embodiment of the present invention, the apparatus includes a portable housing having an elongated, non-distensible, flexible member extending therefrom. The elongated member is constructed and arranged for forming a loop-like portion at a first end. The loop-like portion is adapted for releasably encircling a penis about the circumference thereof. The elongated member is slidably enclosed within a flexible, non-compressible conduit between the loop-like portion and the housing, the non-compressible conduit being suitably attached to the housing. The elongated member is slidably enclosed within a soft, collapsible sheath along the loop-like portion, whereby changes in the penile circumference result in a displacement of the elongated member within the non-compressible conduit and the soft, collapsible sheath. The sheath is readily detachable from the conduit such that the sheath of the loop-like portion can be readily detached and interchanged with another sheath member, whereby the loop-like portion is effectively detached and replaced in a very efficient, inexpensive fashion.

The preferred embodiment of the invention includes biasing means positioned within the housing and operatively interconnected to a second end of the elongated member within the housing for placing the elongated member in a tensioned condition. Additionally, the preferred embodiment includes means operatively interconnected to the elongated member for exerting a predetermined force on the elongated member by pulling on the elongated member, the force tending to reduce the size of the loop-like portion. A sensing means senses displacement of the elongated member caused by exertion of the above-mentioned force and provides an output signal indicative of the displacement and, accordingly, of penile rigidity, as the penile rigidity will affect the amount of displacement which occurs when the force is exerted on the elongated member. Control means operatively interconnected to the sensing means provides for acquisition of the output signals and storage of penile rigidity and tumescence data represented by the output signals, the control means also providing for activation of the force means at predetermined intervals.

The preferred embodiment of the present invention also enables changes in penile circumference or tumescent activity to be monitored. This is accomplished in the preferred embodiment by placing the elongated member under sufficient tension to ascertain the circumference of the penis but without reducing the size of the penis.

In one embodiment of the invention, the means operatively interconnected to the elongated member for exerting a predetermined force includes a torque motor operatively interconnected to the elongated member for periodically exerting a force on the elongated member sufficient to place the elongated member in tension.

In one embodiment of the invention, the sensing means includes an angular potentiometer operatively interconnected to a drive shaft of the torque motor. Accordingly, as the elongated member is displaced, the potentiometer wiper voltage changes in direct relation to the displacement of the elongated member.

The predetermined force means in one embodiment of the present invention includes the torque motor operatively interconnected to the elongated member. By passing a fixed, predetermined current through the torque motor, the calibrated force is exerted on the loop-like portion encircling the penis. The displacement of the elongated member in response to this calibrated force is a function of the compressibility or rigidity of the penis.

In still another embodiment of the invention, the transducer means monitors penile tumescence only. Additionally, in the preferred embodiment of the present invention, a second transducer is mounted within the housing to permit concurrent usage of loop-like portions whereby penile base and tip portion rigidities can be concurrently tested.

The present invention is particularly advantageous in that in the preferred embodiment it provides for continuous monitoring of penile tumescence and further provides for measurement of penile rigidity throughout the tumescent event. Accordingly, the present invention provides a trace or record of the tumescence and rigidity at various times throughout the penile tumescent event and provides for measurement of rigidity duration.

Furthermore, the present invention is ambulatory, enabling its use at a remote site, such as a patient's home, away from the hospital. Accordingly, the testing or screening can be performed with very little impact on a person's daily routine or schedule by not requiring that the subject stay overnight in a health care facility. Additionally, the present invention in its simplest form requires little support equipment, special facilities or support personnel. Thus, the present invention provides a simple but effective and accurate technique for monitoring penile rigidity and tumescence during penile tumescent events while a person is sleeping at home. Additionally, sine there is no tape, intravenous tubing, or other complicated attachments to the body, there is no discomfort or risk to the patient, thereby allowing the patient to attain a restful night'sleep while the testing is performed.

In the preferred embodiment, the present invention further includes a central processing unit programmed with an algorithm so as to be capable of detecting patient tampering thereby greatly increasing the integrity of the data obtained.

In yet other embodiments of the present invention, the penile tumescence and rigidity monitor includes a data communications link capability so as to permit repetitive nightly testing at home (or at a remote, familiar site) without necessitating personally bringing the collected data to the hospital/clinic for interpretation.

In the preferred embodiment of the present invention, the collapsible, soft sheath along the loop-like portion is detachably interconnected to the flexible, non-compressible conduit. Accordingly, the collapsible, soft sheath along the loop-like portion can be readily detached and interchanged with another collapsible, soft sheath, thereby effectively enabling detachment and replacement of the loop-like portion as regards that portion which makes contact with the patient.

In yet another embodiment of the present invention, the flexible, non-compressible conduit between the loop-like portion and the housing is detachable from the housing such that the non-compressible conduit can be readily detached from the housing and replaced.

In still other embodiments, the elongated member is detachable from the housing. In yet other embodiments the elongated member and the non-compressible conduit are both detachable from the housing.

These and various other advantages and features of novelty which characterize the invention are pointed out with particularity in the claims annexed hereto and forming a part hereof. However, for a better understanding of the invention, its advantages, and objects attained by its use, reference should be had to the drawings which form a further part hereof, and to the accompanying descriptive matter, in which there is illustrated and described a preferred embodiment of the invention.

BRIEF DESCRIPTION OF THE DRAWINGS

In the drawings, in which like reference numerals and letters indicate corresponding parts throughout the several views;

FIG. 7 is an enlarged sectional view as seen generally along line 7—7 in FIG. 3; and FIG. 8 is a sectional view as seen generally along line 8—8 in FIG. 7.

DETAILED DESCRIPTION OF A PREFERRED EMBODIMENT OF THE INVENTION

Figure 1:
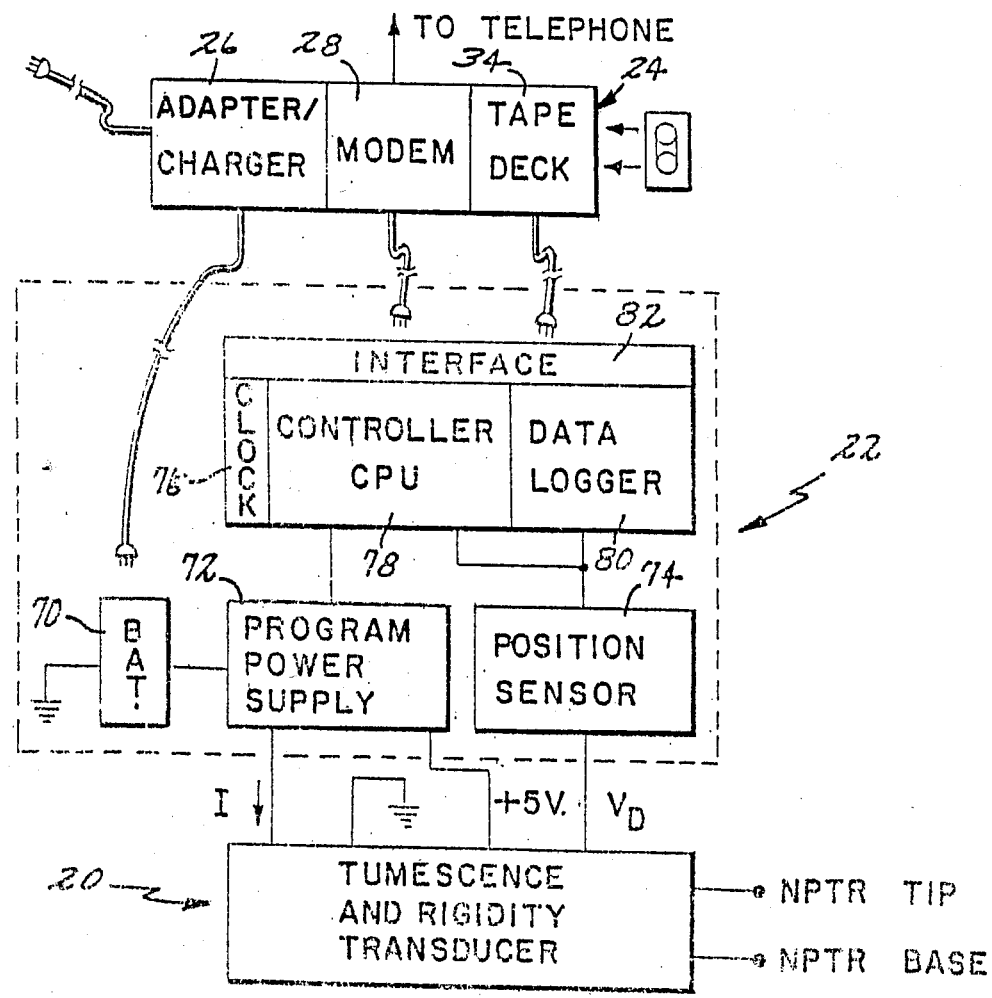
FIG. 1 is a diagrammatic view of a preferred embodiment of a penile tumescence and rigidity monitor in accordance with the principles of the present invention.
Figure 2:
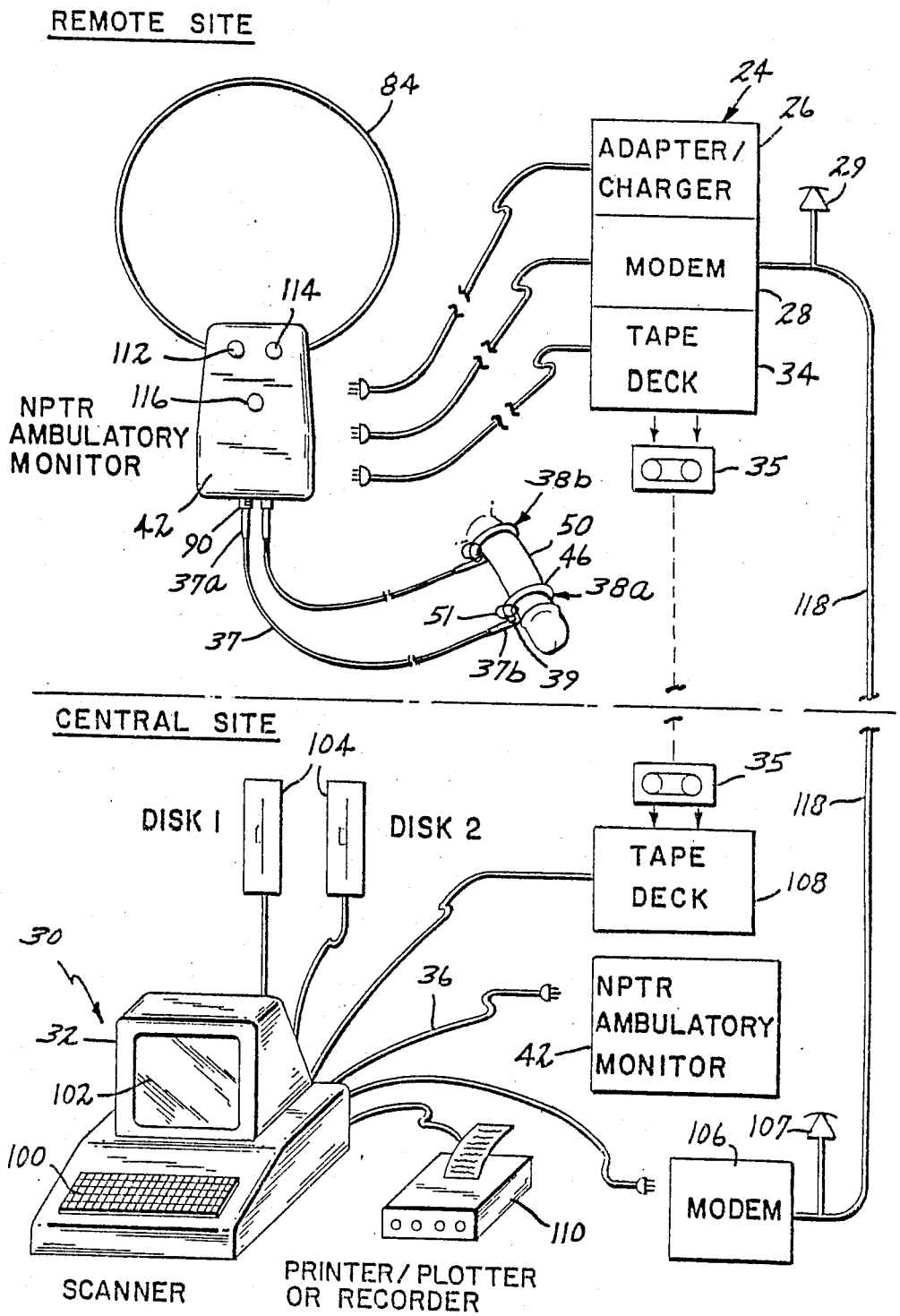
FIG. 2 is an overall diagrammatic view of various communications links between an embodiment of the present invention at a remote location and a programmable scanner apparatus and its associated peripherals at a central location.

Referring now to the drawings, there is diagrammatically illustrated in FIG. 1 an embodiment of a nocturnal penile rigidity and tumescence monitor apparatus in accordance with the principles of the present invention, the embodiment including a transducer apparatus for measuring penile tumescence and rigidity and for providing output signals indicative of the penile rigidity and tumescence, generally referred to by the reference numeral 20, and a control apparatus 22 operatively interconnected to the transducer apparatus 20 and providing for control over the transducer apparatus 20 function and for the logging or storage of penile tumescence and/or rigidity data collected by the transducer apparatus 20. The transducer apparatus 20 and the control apparatus 22 make up the ambulatory nocturnal penile tumescence monitor of the present invention. As further illustrated in FIG. 1, the preferred embodiment of the control apparatus 22 may be operatively interconnected to a peripheral housing 24, preferably including an adaptor/charger 26 enabling the control apparatus 22 to be recharged by plugging the adaptor 26 into a conventional 110 volt alternating current outlet. Additionally, in the preferred embodiment, the peripheral housing 24 is shown as including a modem 28 enabling transfer of data from the nocturnal penile rigidity and tumescence monitor apparatus to a remotely located system scanner 30, preferably including a programmable central processing unit such as a personal computer 32, as generally illustrated in FIG. 2. Additionally, the peripheral housing 24 might also include a tape deck 34 enabling data to be recorded on a cassette and then hand-carried to the central system scanner station. As illustrated in FIG. 2, the penile rigidity and tumescence monitor apparatus 20 might also include a direct connect between the control apparatus 22 and the system scanner 30, as generally illustrated by the direct connection 36.

Figure 3:
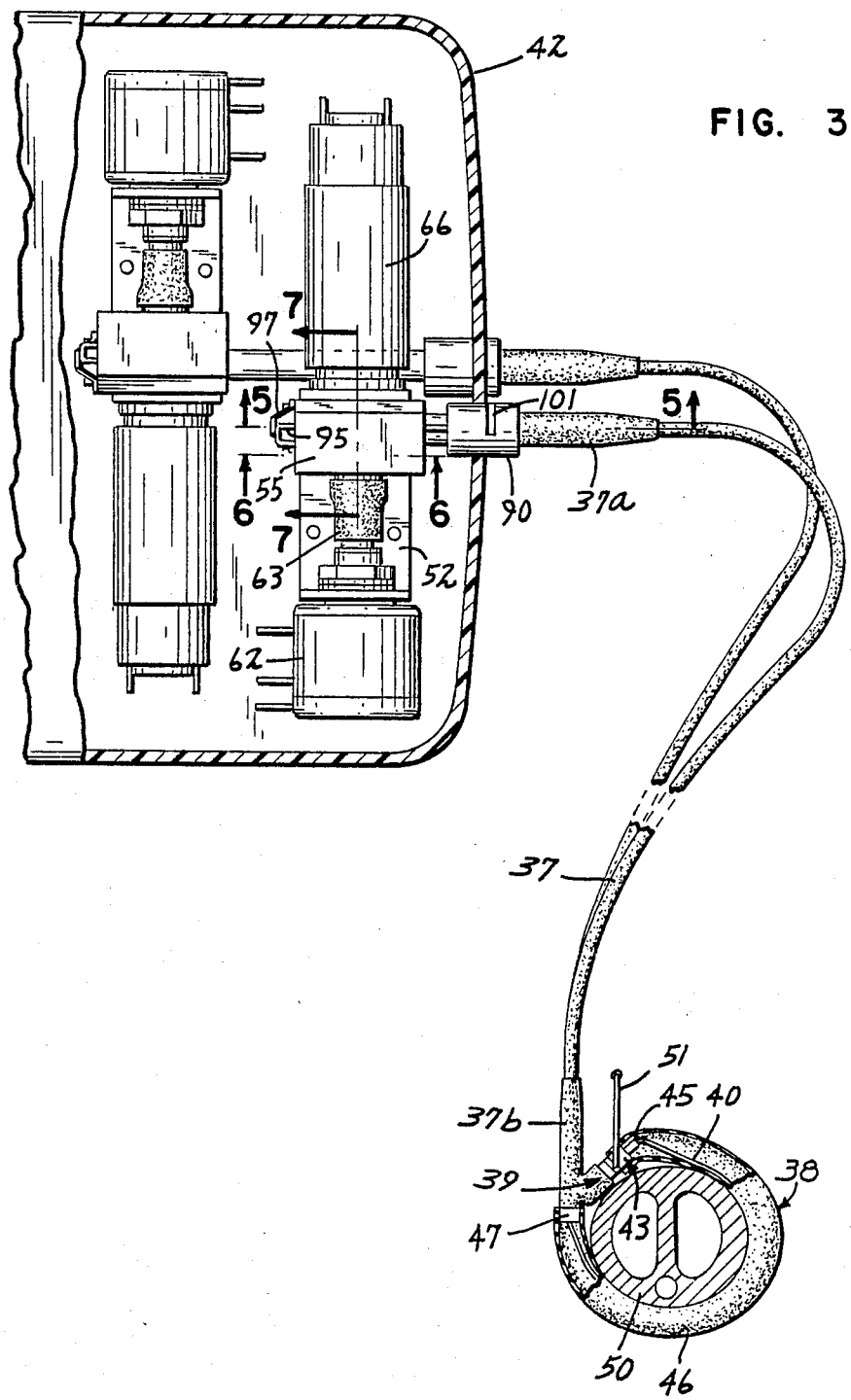
FIG. 3 is a fragmentary plan view of an embodiment of the present invention with portions thereof broken away and shown in section.
Figure 4:
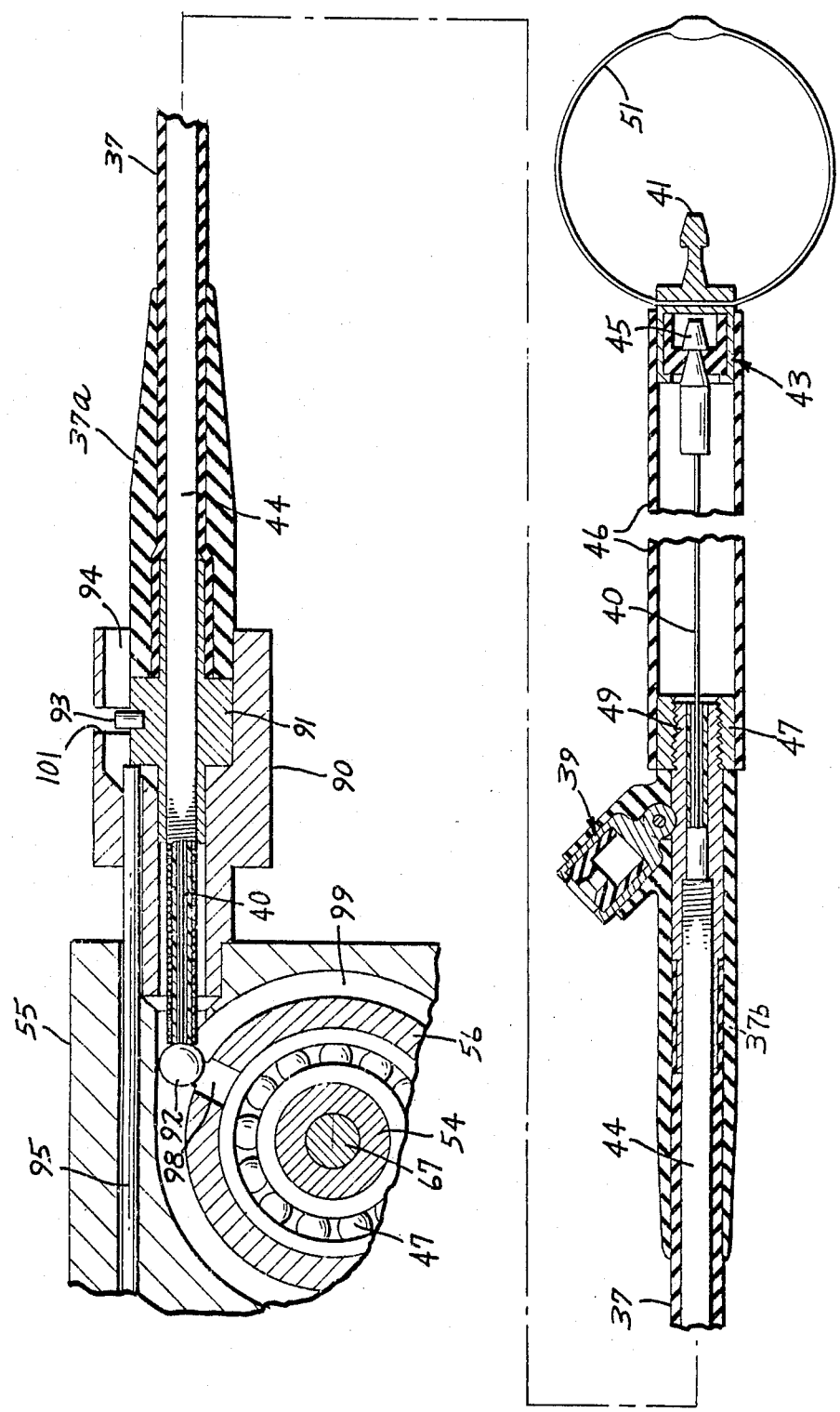
FIG. 4 is a sectional view as seen generally along the longitudinal axis of the elongated member of FIG. 3.

More particularly, as illustrated in FIG. 4, the transducer apparatus 20 of the preferred embodiment includes an elongated member 40, preferably a polymer coated, woven, non-distensible, cable which extends from a housing 42. (While throughout, reference is made to a single elongated member and loop-like portion, it will be appreciated that the preferred embodiment of the present invention includes two such elongated members and loop-like portions 38a, 38b, as generally illustrated in FIGS. 1 through 3 so as to provide for testing of the tip and base portions of the penis. Moreover, each of the elongated members 40 in the embodiment shown are interconnected to a separate motor, pulley and potentiometer arrangement in the housing 42.) The elongated member or cable 40 is slidably enclosed within a flexible, non-compressible conduit 44, also referred to as a tensioning guide, and a soft, collapsible sheath 46 near a distal end thereof. When used, the flexible, elongated member 40 and the sheath 46 are looped back so as to form a loop-like structure 38 for positioning around the circumference of a penis 50. Due to the longitudinally collapsible or compressible nature of the sheath 46 and the non-compressible nature of the conduit 44, the size of the loop-like portion 38 will vary as the elongated member 40 is displaced. As illustrated in FIG. 4, the sheath 46 includes a metal male connector 41 fixedly secured to the sheath 46 at a distal end thereof and a female socket connector 43 facing toward the inside of the sheath 46. The male connector member 41 is configured and arranged to interconnect with a female connector 39 mounted proximate the distal end of the conduit or tensioning guide 44 when the sheath 46 is looped back on itself so as to form the loop-like structure 38. The female connector 43 is configured to connect with a male connector 45 crimped onto the end of the elongated member 40 passing through the conduit 44. The proximal end of the sheath 46 has a metal female connector internally threaded so as to threadably interconnect with a corresponding externally threaded male member 49 proximate the distal end of the conduit 44. The aperture in the female connector 47 is large enough to enable the male connector 45 on the end of the elongated member 40 to pass therethrough. Interconnected to the female connector 41 is a loop-like member 51.

The sheath 46 is positioned on the end of the conduit 44 by threading the male connector 45 on the end of the elongated member 40 through the length of the sheath 46. Using finger pressure through the sheath 46 or a special tool adapted for such purpose, the metal connector 45 is pressed into the female connector 43 until it is engaged. The threaded connector member 47 is then threaded onto the end of the threaded member 49, whereupon the assembly is complete. The loop-like portion is then formed by looping the elongated member 40 and sheath 46 back on itself and inserting the male connector 41 into the female connector 39.

The sheath 46 can be removed from the elongated member 40 by unthreading the threaded member 47 from the threaded member 49. The threaded end portion of the conduit 44 is then grasped, i.e., with two fingers of one hand, and the loop-like portion 51 is grasped in one or two fingers of the other hand, whereupon the conduit 44 and the loop-like portion 51 are pulled apart until the male connector 45 is disconnected from the female connector 43.

The loop-like portion 51 can be used as a safety loop to release the loop-like structure 38 if necessary, thereby preventing any inadvertent injury to the penis.

As illustrated in FIG. 4, the conduit 44 is suitably enclosed within biologically inert sheaths 37, 37a and 37b. The sheath 46 is also preferably biologically inert.

Figure 5:
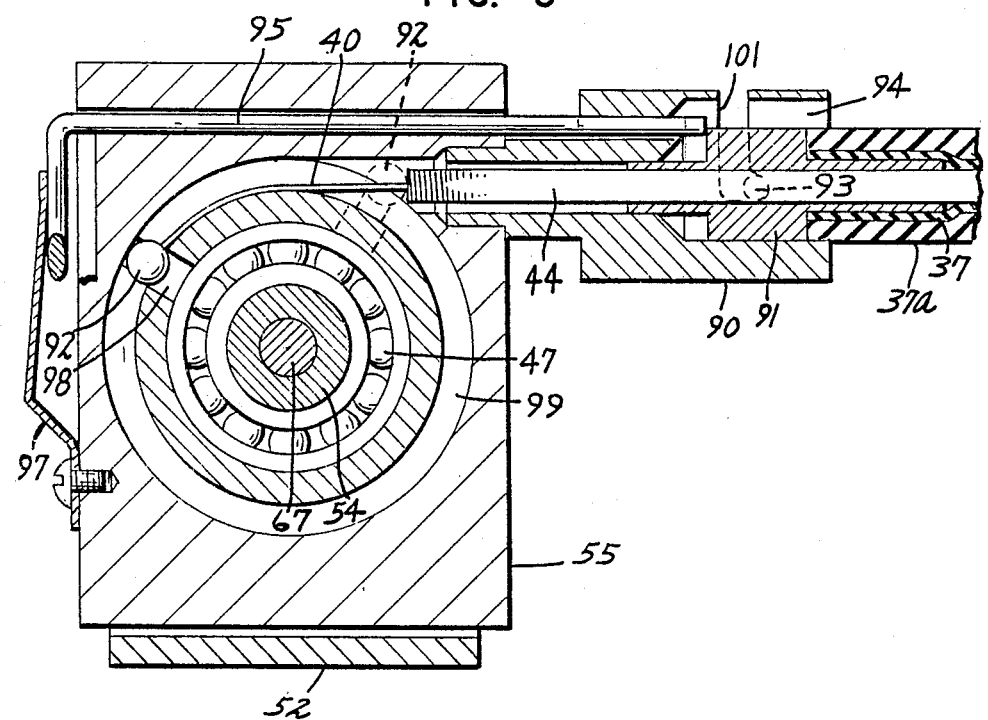
FIG. 5 is an enlarged sectional view as seen generally along line 5—5 in FIG. 3.
Figure 6:
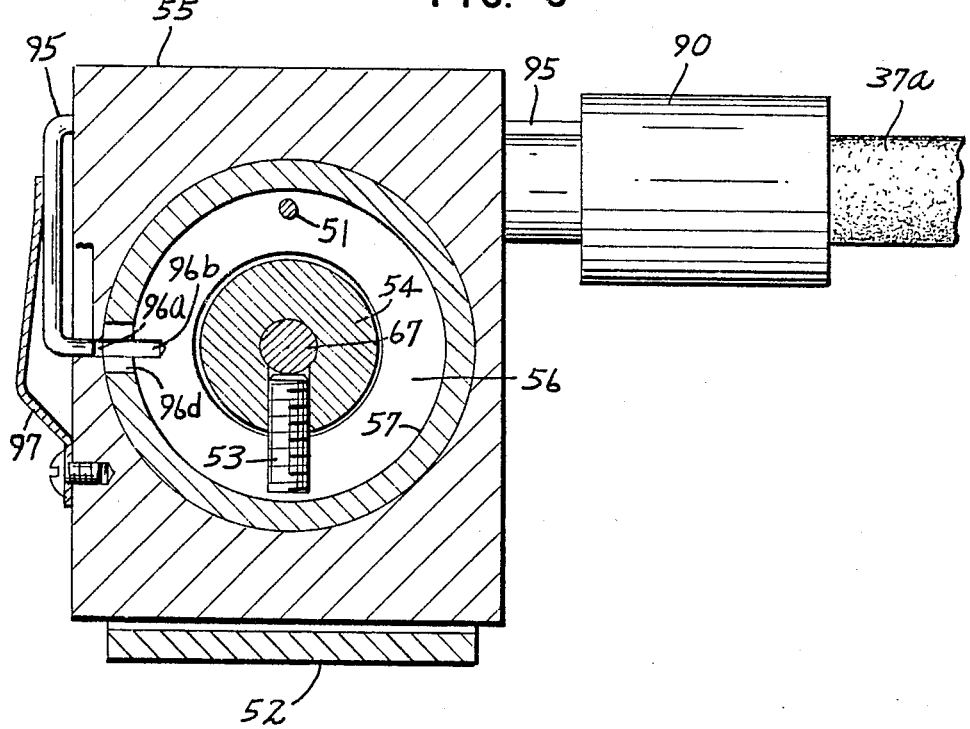
FIG. 6 is an enlarged sectional view as seen generally along line 6—6 in FIG. 3.

As illustrated in the embodiment shown in FIG. 3, mounted inside of the housing 42 is a torque motor 66 whose drive shaft 67 is interconnected to an angular potentiometer 62 by a flexible tubing 63. Although the torque motor 66 and the angular potentiometer 62 are generally aligned, the flexible tubing 63 allows for some misalignment. The torque motor 66 and the angular potentiometer 62 are suitably supported in the housing 42 by a bracket 52 fixedly secured in the housing 42. As illustrated in FIGS. 5–8, intermediate of the torque motor 66 and the potentiometer 62 is a drive wheel member 54, also referred to as a drive pulley member, and a cable wheel member 56, also referred to as a cable pulley member. The drive wheel 54 and the cable wheel 56 are in turn mounted within a bore of a rectangular housing 55 which in turn is suitably connected to the bracket 52. The drive wheel 54 is fixedly interconnected to the drive shaft 67 by a threaded pin 53 which is threaded into a cylindrical bore correspondingly threaded on the inside surface thereof so as to engage the drive shaft 67. A bearing assembly 47 is press-fitted onto the drive wheel 54 and the cable wheel 56 so as to enable relative rotation between the drive wheel 54 and the cable wheel 56. As illustrated in FIGS. 6–7, the cable wheel 56 further includes a longitudinally projecting pin member 51 positioned in an inner groove 57 of the cable wheel 56. The pin member 51 and the threaded locking pin 53 cooperate such that the locking pin 53 engages the pin 51 after the drive wheel 54 has been rotated a distance, whereupon the drive wheel 54 and the cable wheel 56 rotate together as the drive shaft 67 rotates. However, when the threaded locking pin 53 and the pin 51 are not in engagement, as illustrated in FIG. 6, the cable wheel 56 is allowed to rotate freely of the drive wheel 54. Accordingly, the threaded locking pin 53 and the pin 51 function as a clutch mechanism to disengage the wheels 54 and 56 when not in contact such that the wheels 54 and 56 can rotate independently of each other and further function to engage the wheels 54 and 56 such that the wheels 54 and 56 rotate together, whereby the pin 53 serves as a driving member and the pin 51 serves as a driven member. In FIG. 6, for example, the wheels 54 and 56 are shown in a disengaged state. As illustrated in FIG. 8, access to the locking pin 53 is obtained through the apertures 96c in the housing 55 and 96d in the cable wheel 56.

The potentiometer 62 is interconnected to the cable wheel member 56 by the flexible tubing 63 which is slid over a projecting collar portion of the cable wheel 56. The potentiometer 62, detects angular displacement of the cable wheel 56. As previously discussed, the flexible tubing 63 allows for misalignment of the potentiometer and motor shafts while creating no forces on the cable wheel 56 which would interfere with the free rotation of the cable wheel 56.

The above described design enables the forces exerted on the elongated member 40 to be transmitted directly through the cable wheel 56 to the drive motor shaft 67 by way of the bearing assembly 47 and the drive wheel 54. Although not shown, the motor shaft 67 is suitably supported by bearings in the motor housing, thereby providing maximum support and concentricity to all parts. The cable wheel groove 57 is radially aligned over the bearing assembly 47, the threaded locking pin 53 engages the pin member 51 generally in alignment with the groove, and the cable groove 57 is longitudinally positioned as close as possible to the bracket 52 on the motor side in an effort to reduce friction and torque in the motor bracket assembly. As the cable wheel 56 rotates due to displacement of the elongated member 40, the potentiometer 62 is turned, providing an indication of the loop diameter.

As illustrated in FIG. 4, the conduit 44 is removably interconnected to a mounting member 90 of the housing 55 by a metal bayonet fitting 91, the mounting member 90 being suitably secured to the housing 55 and defining a passageway for removable receipt of the bayonet fitting 91 and the conduit 44. The elongated member or cable 40 has a spherical member 92 attached to its end and extending beyond the conduit 44 so as to serve as an anchor for anchoring the elongated member 40 in the cable wheel 56. The bayonet fitting 91 is fixedly connected to the conduit 44 intermediate the ends thereof, an end of the conduit extending beyond the bayonet fitting 91 and extending into a passageway of the housing 55 adapted to removably receive the conduit 44 and the spherical member 92. The conduit member 44 and the elongated member 40 assembly are attached to the cable wheel housing 55 by inserting the bayonet fitting 91 into the connector member 90. A radially extending pin 93 of the bayonet fitting 91 slides along a slot 94 in an inner wall of the connector member 90 such that the bayonet connector 91 engages an engagement pin 95, which is normally biased into apertures 96a of the cable wheel housing 55 and 96b of the cable wheel 56 by a spring tension member 97, which is mounted on the cable wheel housing 55 such that the engagement pin 95 is forced out of the groove 96b of the cable wheel 56, therby allowing the cable wheel 56 to freely rotate. As the spherical member 92 leaves the end of the conduit 44, it is forced into an aperture or seat 98 of the cable wheel 56 and an outer groove 99 of the cable wheel 56. As the cable wheel 56 rotates, the metal spherical member 92 is retained in the seat 98 of the outer groove 99 as generally illustrated in FIG. 5. As the pin 93 of the bayonet fitting 91 reaches the end of the slot 94, it is rotated ninety degrees to the side and released such that it is forced into a longitudinally extending groove portion of an L-shaped groove 101 of the bayonet fitting 91, as generally illustrated in FIG. 5 in phantom line. Thus, the elongated member 40 and its associated tension guide 44 are attached to the cable wheel housing 55. Additionally, the elongated member 40 is attached to the cable wheel 56 by the spherical member 92. Additionally, the engagement pin 95 is removed from the aperture 96b of the cable wheel 56 such that the cable wheel 56 is free to rotate. As illustrated in FIG. 3, the connector member 90 and the bayonet fitting 91 are readily accessible from outside the housing 42 such that the tension guide 44 and cable 40 can be readily detached and replaced.

The cable 40 and tension guide 44 assembly is removed from the cable wheel housing 55 by first fully extending the loop-like portion 38 so as to pull on the cable, thereby rotating the cable wheel 56 and bringing the spherical member 92 to the end of the conduit 44. While keeping tension on the loop-like portion 38 and thus the cable 40, the bayonet fitting 91 is pressed inward, rotated ninety degrees counter-clockwise and released. The tension guide 44 and cable 40 are then removed from the connector member 90. As the tension guide 44 and cable 40 are removed, the engagement pin 95 is released, which then locks the cable wheel 56 in position for subsequent re-insertion of the cable assembly.

The angular potentiometer 62 might be a 10K precision device with a plus five volt reference voltage. Any displacement of the elongated member 40 caused by changing penile circumference results in a change in the potentiometer wiper voltage in direct relation to the elongated member's displacement. Accordingly, the potentiometer 62 provides a continuous reading of the penile tumescence activity.

The motor 66 might be a DC torque motor which includes a zero to five amp. variable direct current supply. By passing a fixed, known current through the torque motor when the tumescence occurs, a calibration force can be exerted on the loop-like portion of the elongated member 40 encircling the penis. The resultant cable displacement in response to this calibrated force is a function of the compressibility or rigidity of the penis. By repetitively cycling the motor current at timely intervals, a regular sampling of penile rigidity obtained during a penile tumescent event is obtained. The torque motor 66 might be activated at varying intervals, so as to apply a force sufficient to place the cable 40 in a predetermined tension. After each sampling interval, the motor 62 is preferably reversed such that the threaded locking pin 53 is disengaged from the pin member 51 as generally illustrated in FIG. 6. This frees the cable 40 so as to loosen the loop-like portion 38 and allow the cable wheel 56 to be rotated by pulling on the cable 40 when one wishes to remove the cable 40 and tension guide 44 from the housing 42.

The outputs of the transducer apparatus 20 are the DC motor current representative of the motor torque developed and the potentiometer wiper voltage representing loop displacement and penile circumference change.

In use, the end of the elongated member 40 is positioned around the circumference of the penis so as to form the loop-like portion 38 thereabout. The torque motor 66 will periodically apply a slight tension to the elongated member 40 by rotating the cable wheel 56 sufficient to overcome any resistance in the drive assembly and system friction, but not sufficient to compress a flaccid penis. As penile circumference changes, the displacement of the elongated member 40 will change. The potentiometer wiper voltage changes in direct relation to displacement of the elongated member 40. To measure rigidity, a fixed, predetermined current might be passed at predetermined intervals through the torque motor 66 when tumescence is detected, so as to exert a calibrated force on the loop-like portions 38 encircling the penis having a tendency to compress the diameter of the penis. The cable displacement in response to this calibrated force is a function of the compressibility or rigidity of the penis. Repetitive cycling of the motor current at timely intervals provides a regular sampling of penile rigidity obtained during a penile tumescent event.

As illustrated in FIG. 1, the control apparatus 22 is operatively interconnected to the transducer apparatus 20 to provide a zero to five amp variable direct current supply to the torque motor 66 and a plus five volt reference voltage for the potentiometer 62. As illustrated in FIG. 1, the control apparatus 22 might include a DC battery power source 70 such as two DC batteries, a power supply 72, a position sensor 74, and an electronic control unit including an internal clock 76, a programmable central processing unit 78, a data logger or memory unit 80 which will preferable include a memory backup, and an interface unit 82. The battery power source 70 provides the power for the power supply 72 which in turn provides the direct current to the torque motor 66 and the plus five volt reference voltage for the potentiometer. The position sensor 74 senses the potentiometer wiper voltage indicative of loop displacement and penile circumference change. The internal clock 76 is utilized to determine the time and date that various events occur while the central processor unit 78 provides for control over the power supply 72 and the storage of penile rigidity and tumescence data in conjunction with the data logger 80. The interface unit 82 enables interface communications with the modem 28 and/or the tape deck 34 and any other peripheral equipment as required. Accordingly, the control apparatus 22 performs all transducer apparatus control, data acquisition and storage, and peripheral interface communications.

The transducer apparatus 20 and the control apparatus 22 are preferably contained within the same portable mounting frame. Additionally, the mounting frame or housing 42 is configured such that the nocturnal penile tumescence and rigidity monitor is ambulatory in that it performs data acquisition of all specified physiological inputs while belted or strapped to the patient. A possible configuration is illustrated in FIG. 2, wherein a belt 84 is illustrated as being attached to the housing containing both the transducer apparatus 20 and the control apparatus 22.

Complete and unquestionable operation of the control apparatus of one embodiment of the present invention implemented to perform monitoring of tumescence and rigidity with the monitor electromechanical hardware is as follows:

1. Penile loops are comfortably fitted at the base and at the tip of the penis—these will act as the devices that displace circumferences and establish the quantities of tumescence and rigidity.

All sampling action occurs on a 15 second interval which consists minimally of a tumescence measurement, mild loop force tensioning and motor back off. The processes of mild tensioning, block rotor, and backoff in that order specifically define "tugging." If tumescence has exceeded a minimum threshold value, the sampling action consists of tumescence measurement, mild loop force tensioning, strong loop force tensioning, rigidity measurement and motor backoff.

2. Sampling is an iterative process performed on a 15 second interval in synchrony from time-zero when the monitor switch was turned on. At time-zero sample zero is taken, it is unique because tumescence and rigidity are sampled regardless of the relative value of tumescence. It is referred to a the "initialization sample." Sample 1 is 15 seconds later, Sample 2 is 30 seconds later, etc. The "sample count" (as this interval count is referred to) reflects an even or odd value.

On all odd sample counts, only tumescence is sampled. On even sample counts, tumescence and tugging occurs, and rigidity sampling may also occur if and only if tumescence has exceeded a threshold value. Another perspective of the sampling procedure is that tumescence is sampled every 15 seconds; tugging occurs every 30 seconds and rigidity is sampled every 30 seconds only if tumescence has exceeded a minimum calculated threshold value.

3. Data pertinent to tumescence and rigidity is stored in a "session" format—a session is a time quantification of a nocturnal monitoring period limited to 10 hours in duration. The start and stop times associated with this period are stored and every data sample contained therein is in synchrony with the 15-second sample period throughout the session. Circumference (tumescence) of the penile base and tip loops is sampled and stored in CMOS RAM, cassette tape, bubble or nonvolatile memory every 15 seconds along with time and date. Rigidity (hardness) of base and tip is sampled every 30 seconds (in synchrony with tumescence sampling) only when tumescence has reached a specified 6 mm (adjustable set point) threshold above the minimum tumescence, otherwise it is not sampled. The minimum is defined as the minimum tumescence value incurred up to and including that sample time and is stored as such until another value smaller than it replaces it. The resultant threshold is thus dynamically altered to maintain an accurate reference for the triggering of rigidity sampling.

4. Tumescence sampling (during even and odd sample counts) is for all intents and purposes a passive measurement, but requires mild contact to be accurate. The loop action emulates a constant tension tracking capability, wherein it must be tightened mildly (every 30 seconds in even samples) then released such that it relaxes to a low contact force state at which time tumescence can be measured. This mild loop force tensing action defined as "tugging," is implemented by turning on the torque motor 66 with a minimum current resulting in a mild loop-capable pull force. This force is transferred radially to the penile shaft tissue which resists compression of the loop by the state of its existing hardness. When the motor shaft rotation rate (signalled by the shaft-couple-potentiometer) reaches a state of minimal travel per unit time (adjustable set point), block rotor is attained and the torque motor is then supplied reverse current for a specified time (adjustable interval) to rotationally back off and release tension on the loop cable. The processes of mild tensioning, block rotor, and backoff in that order specifically define "tugging."

5. Rigidity sampling (during even sample counts only) is in interactive measurement by which a prescribed amount of force is actively applied to the loop cable until a resultant condition has been attained. For rigidity sampling to occur, tumescence (meaured at the start of this even sampling period) must exceed the threshold tumescence (minimum circumference plus 6 mm). When it does, the data sampling procedure for this even sample takes place as follows. Tumescence (circumference) is measured at the start of the cycle and the mild loop force action is applied—at its block rotor state, a strong current is programmed to the torque motor 66 resulting in a strong loop cable pull force. When the motor shaft rotation (signalled by the shaft-coupled potentiometer) reaches a state of minimal travel per unit time (adjustable set point); block rotor is attained. At this state circumference is meaured (that value with respect to the tumescence circumference is referred to a rigidity) and stored as rigidity, and the torque motor 66 is supplied reverse current for a specified time (adjustable interval) to rotationally back off and release tension on the loop cable. The processes of circumferential (tumescence) sampling, mild tensioning, strong tensioning, circumferential sampling (representative of rigidity) and backoff—in that order—define "rigidity sampling."

As disclosed in U.S. Pat. No. 4,515,166 and Ser. No. 713,452, and as illustrated in FIG. 2, the nocturnal penile rigidity and tumescence monitor apparatus is utilized in conjunction with a system scanner 30 which is based around a programmable processor such as a personal computer. The system scanner 30 enables the setting of adjustable parameters on the control apparatus 22, provides for analysis of penile rigidity and tumescence data, and provides for support and hard copy print out. It is anticipated that the system scanner 30 will reside at the clinic or other central site and collect the incoming data from various remote patient sites.

Preferably the personal computer 32 is user friendly with extensive use of menus on a CRT to provide operator instruction and guidance. Preferably, the system scanner with its personal computer 32 and various peripheral equipment will provide the following functions:

1. Monitor initialization, including preparation for patient use, self-testing, entering of patient name, entering of patient I.D., updating of the date/time, entering of the monitor apparatus serial number, presetting all adjustable values utilized by the algorithm programmed into the control apparatus 22.

2. Calibration of the nocturnal penile and tumescence rigidity monitor apparatus, including recording the data together with the time and date obtained by running one torque motor cycle after fitting a loop to a patient's penis.
3. Down-loading of nocturnal penile tumescence and rigidity monitor data from the control apparatus memory (random access memory (RAM)), the tape deck, and/or the modem which would automatically retrieve session data stored in the control apparatus 22 or the tape unit 34.
4. Data analysis and print-out including analyzing and constructing in usable form for storage and hard copy print-out, penile rigidity and tumescence data of a session or a singular event analysis. Preferably, optional outputs available from this function would include one or all of the following:
    (a) 2D graphic (CRT or hard copy) output for time versus tumescence/rigidity plots.
    (b) 3D graphic (CRT or hard copy) output of time versus tumescence versus rigidity plots for singular events or entire sessions.
    (c) Archive data on tape for later recall without reanalysis.
5. Collection of data from multiple field units by storing data from a particular field unit when polling the field unit via the modem. Preferably the time report sequence of the field units would be preprogrammed into the control apparatus 22 during the calibration mode.

In order to provide the above specified functions, the system scanner 30 will require additional peripheral equipment in addition to the personal computer 32. The personal computer 32 will preferably include adequate memory, for example 64K to 256K, a keyboard 100 and a high resolution graphics CRT 102. In the preferred embodiment shown, two disk drives 104 are also utilized, however, one may be sufficient for lower use installations. A modem 106 positioned either internally of the computer or externally as shown in FIG. 3, will be required at the central site to provide communications with the modem 28 at the remote site. As illustrated in FIG. 3, the modems 28 and 106 typically will be interconnected either directly or acoustically to telephone sets, illustrated by reference numerals 29 and 107. The telephone sets 29 and 107 will, in turn, typically be interconnected by a conventional voice grade telephoneline 118. In addition, if the remote site utilizes the tape deck 34 or data transfer, a corresponding tape deck 108 will be required at the central site. For hard copy or print out purposes, a printer and/or plotter 110 will be required. Corresponding RS232C interface capabilities will preferably be utilized for the tape deck 108 and the printer and/or plotter 110 interfaces. Additionally, a parallel interface capability might be present for future enhancements of the system scanner. The various hardware elements of the system scanner might have disk desk top configuration optimized for minimal area occupancy.

In addition to the hardware requirements, the software will include appropriate operating system software, various utility software such as tape, modem, multiplexer mode, plotter, and CRT dump capability, and various interface software providing for calibration, downloading and direct hookup of the nocturnal penile and tumescence rigidity monitor to the computer 32 to enable real time data transfer for real time functional verification of the tumescence and rigidity monitor. In addition, software providing for data analysis and number crunching will also be required. For output purposes, 2D and 3D graphic software may be required as well as report form generation software enabling patient data, session data and graphic summaries for hard copy patient reporting. In addition, it is preferred that there be interactive user operation of software for menu selected CRT graphics, data analysis options and printout. As a further support measure, it is preferred that the software also provide for patient file bookkeeping, enabling the patient's files to be updated.

One possible alternate embodiment of the present invention is the use of a chart recorder in place of or in addition to the system scanner. The chart recorder will include an analog chart recorder or a dot matrix printer preferably utilizing standard sized paper. Either a serial RS232C interface (if digital) or an analog specified interface (if analog) to the nocturnal penile tumescence rigidity monitor apparatus will be provided for interconnection of the chart recorder to the potentiometer output of the monitor apparatus. Accordingly, the chart recorded will be capable of providing a hard copy of the tumescence data in the real time or at the completion of a session. The chart recorder will preferably be capable of multichannel operation. While the chart recorder as currently envisioned will provide only 2D graphics capability, it will be of minimal size enhancing portability.

Typically, use of the nocturnal penile tumescence and rigidity monitor apparatus will include a scenario having the following phases of operation:
1. Patient introduction and monitor initiation.
2. Patient monitoring session.
3. Transfer of session data.
4. Data analysis and reporting.

Prior to patient introduction to the monitor apparatus, the control apparatus 22 battery is charged; or disposable batteries replaced and the monitor apparatus is interconnected to the system scanner 30 for initialization to enter the patient's name, I.D. number, date/time, modem dial time for automatic reporting, and modem serial number. This information is entered via the keyboard 100. The initialization information is also stored in the scanner disk patient file for recall and recombination with the collected session data. From this point on, the monitor apparatus need not be attached to the system scanner 30. The patient is introduced to the monitor apparatus by demonstrating monitor calibration and operation. Monitor calibration is performed by placing the monitor loops 38 around a built-in calibration cylinder and pressing a calibration function key 112 on the housing 42 of the monitor apparatus. Upon pressing the calibration function key 112, the monitor apparatus will take a tumescence and rigidity sample. Force/displacement constants are derived based on the known force applied and the known rigidity of the calibration cylinder. The constants are then stored internally for the force displacement transfer function for determining tumescence and rigidity. The monitor loops 38 are then placed around the patient's penis for finger printing. When the calibrate function key is again pressed, the monitor will take a tumescence and rigidity sample which is stored and identified as a finger print of that patient's characteristics. The monitor will continue to sample once a minute until the stop function key 114 on the housing 42 is pressed at which time the monitor will shut itself off. (The calibration function key 112 initiates the monitoring functions while the stop function key 114 terminates the functions.) This exercise serves a twofold purpose; patient instruction and security for maintaining patient integrity. The monitor is then detached and given to the patient for home use over a predetermined length of time, e.g. one to five nights of recording.

The patient will calibrate, attach and wear the monitor for consecutive nights until the necessary data is collected. Singular nocturnal session data may be downloaded to tape or to modem daily by simply connecting the monitor to the peripheral box 24 containing the tape deck 34, modem 28 and the AC adapter/charger 26 on awakening. This will transfer the data collected and recharge the monitor's battery. Session disruption or patient notations can be made with a patient activated event marker function key 116 on the housing 42. Upon pressing the event marker function key 116, the date and time is recorded. The patient should then record in a separate log or diary, the reason for the session disruption. This will facilitate interpretation of the data upon being returned to the clinic or other central site. Should the battery be weak or dead, the monitor may be connected to the AC adapter/charger 26 via a suitable cord connector. While the unit is no longer amubulatory at this point, this is not expected to be the normal operating procedure and should be avoided when possible.

After having collected the data, the data is transferred to the central system scanner 30. The monitor apparatus provides flexibility of getting acquired data to the central site (clinic or hospital) in a convenient manner without impacting the "ambulatory" nature of the device. Following are three data transfer possibilities for the nocturnal penile tumescence and rigidity monitor.

One is the traditional cassette tape transfer which is proven reliable but somewhat clumsy. The problem is the size of the tape transport; it greatly increases the ambulatory monitor's size. It also requires more battery backup (even though it isn't "on" that often in the course of moni-tor session), and that increases battery size and weight. So its integration into the ambulatory monitor for data storage is unlikely if the monitor is to remain "ambulatory" in the true sense of the word (which implies light weight, small and comfortable). The tape deck 34 will be housed in peripheral housing 24 with the battery charger/AC adapter and modem. This configuration requires daily downloading of the monitor data on tape in final archival form. The tape, represented by reference numeral 35, would then be handcarried to the system scanner 30. The monitor needs provisions for only one session of data storage. However, if semiconductor storage density is utilized (such as with 2KBYTE or 8KBYTE bit CMOS Static RAM IC's) in the unit itself sufficient for 3 monitor sessions, the peripheral box 24 may only be necessary for power support, and data would transfer inherently with return of the monitor to the central site and then be down loaded directly into the system scanner 30.

The second transfer option is the use of the modem 28, or modulator-demodulator for telephone data communications. The modem, because of size, may also be required to reside in the peripheral box 24 with the tape deck 34 and the adapter/charger 26. Its support would be to provide daily update to the clinic of patient data and operational verification of the monitor. This role may eliminate the need for field tape support. The data would be archived on tape or disk at the central site. The patient would connect the monitor to the peripheral box 24 at the conclusion of the monitor session. Preferably, auto modem control would take over for the whole reporting process.

The third transfer option downloads the data from the monitor to the system scanner 30 via direct connection. This is possible when all sessions are recorded using suitable memory such as solid-state or bubble memory, or when the recording sessions are conducted in close proximity to the scanner site.

Once data is resident in the system scanner 30, analysis may begin. Penile tumescence and rigidity data, patient data, date/time, etc., is analyzed and coordinated to present the final hard copy report. Data is analyzed, formatted and archived on suitable mass storage such as cassette tape for future recall if necessary. The final report might consist of a hard copy of any or all of the following information:

(a) patient data—name, ID number;
(b) date/time;
(c) monitor serial number;
(d) finger print" samples of tumescence and rigidity;
(e) Initialized Thresholds—preset constants in the data analysis equations which may be altered for appropriate reason;
(f) Session Summary—numerical data summary of nocturnal penile tumescence and rigidity events, e.g. max, min, total time, etc., patient activation notations and verbal description of patient;
(g) 2-D Graphics—superimposition of all or any number of data including tumescence and rigidity versus time plots for the tip and base loop portions which might be displayed in two forms, entire session data and individual event data; and,
(h) 3-D Graphics—optional 3-D graphics of entire session or individual events data which are plots of tumescence vs. rigidity vs. time.

It is to be understood, however, that even though numerous characteristics and advantages of the invention have been set forth in the foregoing description, together with details of the structure and function of the invention the disclosure is illustrative only, and changes may be made in detail, especially in matters of shape, size and arrangement of parts within the principles of the invention, to the full extent indicated by the broad general meaning of the terms in which the appended claims are expressed.

What is claimed is:

1. A penile rigidity and tumescence monitor and apparatus, comprising:
(a) transducer means for providing output signals indicative of penile rigidity and tumescence throughout a penile tumescent event, the transducer means including motor means enclosed in a housing and being interconnected to an elongated member for exerting a predetermined force on the elongated member and sensor means for sensing displacement of the elongated member, the motor means including clutch means for releasing tension in the elongated member, the elongated member being slidably enclosed within a non-compressible conduit, the elongated member and its associated non-compressible conduit being interconnected to loop-like portion means for releasably encircling a penis about the circumference thereof, the elongated member being non-destructively removable from the non-compressible conduit, fitting means being present for releasably attaching the non-compressible conduit to the housing of the transducer means, whereby the non-compressible conduit can be interchangeably replaced; and (b) control means interconnected to said transducer means for providing control of said transducer means, said control means further providing for acquisition of said output signals from said transducer means.

2. A monitor apparatus in accordance with claim 1, wherein the loop-like portion means includes a soft, collapsible sheath, the sheath being interchangeably removable from the elongated member and the non-compressible conduit as to enable interchanging of the sheath.

3. A penile tumescence monitor apparatus, comprising:

(a) a housing;

(b) an elongated, non-distensible, flexible member extending from said housing and having proximal and distal ends relative to said housing, said elongated member being slidably enclosed within a flexible, non-compressible conduit along a first portion thereof and slidably enclosed within a collapsible sheath proximate a second portion thereof, said collapsible sheath and said elongated member forming a loop-like portion adapted for releasably encircling a penis about the circumference thereof, fitting means being positioned proximate the proximal end of the non-compressible conduit for removably interconnecting the non-compressible conduit to the housing;

(c) tension means positioned within said housing and interconnected to said elongated member for exerting a predetermined force on said elongated member, said tension means including pulley means driven by motor means, the pulley means including a first cable pulley and a second drive pulley, the second drive pulley being fixedly mounted on a drive shaft member of the motor means for rotation with the drive shaft member, the first cable pulley and the second drive pulley including clutch means enabling independent rotational movement of the first and second pulleys over a predetermined range of motion, the clutch means including first and second means which, upon engagement with one another, cause said first and second pulleys to rotate in unison together, said first and second pulleys normally being positioned in a disengaged state by the motor means, the elongated member including anchor means being positioned proximate the proximal end thereof and configured for removable attachment to and detachment from the cable pulley member;

(d) sensing means interconnected to said cable pulley member for sensing displacement of said elongated member; and (e) control means for providing control of the monitor apparatus.

4. A monitor apparatus in accordance with claim 3, wherein said first cable pulley includes an exterior radially facing groove including seat means for receipt of the anchor means of the elongated member, a frame member circumferentially enclosing the groove and including an aperture adapted to receive the anchor means and the elongated member and extending into the groove from an exterior of the frame member, lock means cooperating with the first cable pulley for locking the first cable pulley in position, whereby the seat means and the aperture in the frame member are aligned when the non-compressible conduit is removed from the housing, thereby enabling the elongated member and its associated anchor means to be removed and inserted as required.

5. A penile tumescence monitor apparatus, comprising:

(a) a housing;

(b) transducer means including motor means interconnected to an elongated member for exerting a predetermined force on the elongated member, and sensor means for sensing displacement of the elongated member and for providing output signals corresponding to the displacement of the elongated member sensed, the motor means including clutch means for releasing tension in the elongated member, the elongated member being slidably enclosed within a non-compressible conduit along a first portion thereof, and slidably enclosed within a collapsible sheath proximate a distal end portion thereof for forming a loop-like portion encircling about the circumference of a penis, anchor means being positioned proximate a proximal end of the elongated member for interchangeably attaching the elongated member to the motor means, the elongated member being non-destructively removable from the non-compressible conduit and the collapsible sheath, the collapsible sheath being interchangeably attached to the non-compressible conduit, the collapsible sheath and the elongated member including cooperating connector means for detaching the collapsible sheath from the elongated member; and (c) control means electrically interconnected to said transducer means for receiving said output signals and providing control of said transducer means.

6. A monitor apparatus in accordance with claim 5, said monitor apparatus includes means for exerting a predetermined force on said elongated member tending to reduce the size of said loop-like portion and cause slidable displacement of said elongated member in said sheath, whereby penile rigidity can be determined from the change in circumference due to application of said predetermined force.

7. A monitor apparatus in accordance with claim 6, wherein said control means also includes a programmed processor means which provides for activation of said force means at predetermined intervals.

8. A monitor apparatus in accordance with claim 7, wherein said programmed processor means includes means for sampling the transducer signal at different rates depending on the degree of tumescence.

9. A monitor apparatus in accordance with claim 5, wherein the cooperating connector means includes a first connector proximate a distal end of said elongated member cooperating with a second connector positioned proximate a distal end of said soft, collapsible sheath, an opposite end of said soft, collapsible sheath being removably threaded into said non-compressible sheath whereby said soft, collapsible sheath can be removed by unthreading said soft, collapsible sheath from said non-compressible sheath and disconnecting said first and second connectors.

10. A monitor apparatus in accordance with claim 5, wherein the non-compressible conduit is interchangeably attached to the housing of the transducer means, whereby the non-compressible conduit can be interchangeably replaced.

11. A monitor apparatus in accordance with claim 5, wherein the elongated member is interchangeably attached at a distal end to the collapsible sheath.

* * * * *

UNITED STATES PATENT AND TRADEMARK OFFICE
CERTIFICATE OF CORRECTION

PATENT NO. : 4,848,361

DATED : July 18, 1989

INVENTOR(S) : Penney et al.

It is certified that error appears in the above-identified patent and that said Letters Patent is hereby corrected as shown below: Title page:

Abstract, line 8, "penil" should be --penile--.

Col. 1, line 29, delete "Methods".

Col. 5, line 2, "sine" should be --since--.

Col. 5, line 5, "night'sleep" should be --night's sleep--.

Col. 7, line 20, "41" should be --43--.

Col. 9, line 11, "therby" should be --thereby--.

Col. 10, line 46, "preferable" should be --preferably--.

Col. 11, line 31, "a" should be --as--.

Col. 12, line 7, "loop-capable" should be --loop-cable--.

Col. 12, lines 22 and 34, "meaured" should be --measured--.

Col. 12, line 36, "a" should be --as--.

Col. 15, line 25, "amubulatory" should be --ambulatory--.

Col. 15, line 41, "moni-tor" should be --monitor--.

UNITED STATES PATENT AND TRADEMARK OFFICE
CERTIFICATE OF CORRECTION

PATENT NO. : 4,848,361

DATED : July 18, 1989

INVENTOR(S) : Penney et al

It is certified that error appears in the above-identified patent and that said Letters Patent is hereby corrected as shown below:

Col. 16, line 22, insert a quotation (") before "finger".

Signed and Sealed this

Second Day of October, 1990

Attest:

HARRY F. MANBECK, JR.

Attesting Officer

Commissioner of Patents and Trademarks